United States Patent [19]
Zunitch et al.

[11] Patent Number: 5,405,330
[45] Date of Patent: Apr. 11, 1995

[54] SYRINGE NEEDLE HOLDER

[76] Inventors: Daniel Zunitch, 11479 Aster St.; Michael L. Wing, 26234 Windsor La., both of Loma Linda, Calif. 92354

[21] Appl. No.: 228,352

[22] Filed: Apr. 15, 1994

[51] Int. Cl.$^6$ ............................................. A61M 5/00
[52] U.S. Cl. ..................... 604/240; 604/264; 604/272
[58] Field of Search ............... 604/240, 239, 241, 242, 604/243, 275, 187, 264, 272

[56] References Cited

U.S. PATENT DOCUMENTS

| 1,503,399 | 7/1924 | Webb . | |
|---|---|---|---|
| 2,034,294 | 3/1936 | Hein | 604/243 X |
| 2,569,901 | 10/1951 | Richard . | |
| 3,884,230 | 5/1975 | Wulff . | |
| 3,994,295 | 11/1976 | Wulff | 604/243 X |
| 4,878,904 | 11/1989 | Callaway . | |

FOREIGN PATENT DOCUMENTS 1076332  2/1960  Germany ............................ 604/241

Primary Examiner—John D. Yasko
Attorney, Agent, or Firm—Richard C. Litman

[57] ABSTRACT

A pivotal syringe needle holder for use with an injector includes a hub and a ball. A needle is supported by the ball which, in turn, is movably supported by the hub so as to permit the needle to be angularly displaced relative to the hub. The hub is engageable with the injector. The ball and hub are configured to form a ball and socket arrangement which cooperatively permits medicant to be communicated therethrough. A contact seal is formed between the ball and hub to prevent loss of medicant therefrom. A physical seal which may be provided supplemental to, or in place of, the contact seal. A needle may be formed as an integral element of a disposable syringe needle holder or a non-disposable syringe needle holder may support a disposable needle. The ball may be manipulated to displace the needle in a desired position relative to the hub and then may be substantially fixed in this desired position. A latch may be provided to releasably fix the ball relative to the hub which, in turn, releasably fixes the needle relative to the hub.

13 Claims, 3 Drawing Sheets

SYRINGE NEEDLE HOLDER

BACKGROUND OF THE INVENTION

1. Field of the Invention

The present invention relates generally to a syringe needle holder and more particularly, to a holder for a syringe needle which permits the syringe needle to be pivotally displaced relative to the syringe barrel.

2. Description of the Prior Art

Fluids are typically be administered to and withdrawn from a patient through a syringe, and the use of a syringe may be limited by its physical characteristics. For example, most syringe needles are rigidly coupled to a syringe barrel. The use of such a syringe within a critical locality may cause an excessive deflection of the needle relative of the barrel and thus break the syringe needle. In an effort to overcome this problem, syringes have been devised to resist the deflection of the syringe needle relative to the syringe barrel.

One such syringe is disclosed in U.S. Pat. No. 2,569,901, issued Oct. 2, 1951 to Ernest N. Richard. The syringe is structured to resist excessive bending as well as limit the penetration of the syringe needle. The barrel of the syringe is received by a sleeve comprising a threaded part for securely holding a ferrule to the nozzle of the barrel. A coupling tube which supports a syringe needle is, in turn, threadably attached to the ferrule. A cursor sleeve which surrounds the needle over a certain length is, in turn, secured to the coupling tube. Parallel to the bottom of the cursor and a predetermined distance therefrom is arranged a ring which forms an extension of the cursor. The ring limits the penetration and resists excessive deflection of the needle.

Although the syringe disclosed by Richard above resists excessive needle deflection and thereby excessive needle breakage, it does not prevent the hazard of needle breakage altogether. In the event that the needle should break, the needle may become separated from the syringe. To address this issue, syringes have been contrived to limit the travel of the needle relative to the syringe.

For example, U.S. Pat. No. 1,503,399, issued Jul. 29, 1924 to John E. Webb, discloses a hypodermic needle and carrier constructed such that the movement of the needle relative to the carrier is limited in the event that the needle breaks away from the carrier. Webb more particularly describes a needle which is secured to an outer end of a needle carrier by solder and in such a manner that if the needle breaks, the needle will break at the solder joint. The needle has a shoulder formed as an enlargement which extends about the needle. A guard fits upon the carrier and includes an abutment shoulder configured such that if the needle should break, the abutment shoulder prevents the needle from passing entirely through the guard.

The use of a syringe may yet remain limited by other factors, such as the confines in which it is to be used. Syringes having a needles which are displaceable relative to their barrels have been produced to administer and withdraw fluids in more restricting areas of application while, at the same time, reduce the risk of needle breakage resulting from the excessive deflection of the syringe needle.

Numerous attempts to present a syringe having a displaceable needle. One such syringe is shown and described in the Webb patent above. Needle carriers of various lengths permit the syringe needles to be extended out of alignment with the syringe barrel.

Another flexible needle and guard device is disclosed in U.S. Pat. No. 3,884,230, issued May 20, 1975 to Goldwyn L. Wulff. Wulff describes a device for reducing the bending and breaking of hypodermic syringe needles. The device includes a flexure tube interconnected between the syringe and needle thus permitting the needle to pivot laterally, and a guard mounted on the syringe and over the needle wherein the guard has a spring disposed therein to bias the needle in axial alignment with the syringe.

Another device which permits the displacement of a syringe needle relative to a syringe barrel is disclosed in U.S. Pat. No. 3,994,295, issued Nov. 30, 1976 to Goldwyn L. Wulff. The device consists of an outer casing or shell and an inner resilient tube. The tube is bonded at one end to a stem adapted for connection to the syringe barrel and at an opposite end to a needle mounting member seated over the end of the shell. Should the needle move, the needle mounting member tends to leave the seat and have displacement relative to the shell.

Yet another syringe having a needle displaceable relative to the syringe barrel is disclosed in U.S. Pat. No. 4,878,904, issued Nov. 7, 1989 to James J. Callaway, who discloses a needle and holder assembly configured such that the needle can be moved between an extended and a retracted position. In a retracted position, the needle and holder junction in substantially rigid. In an extended position, a length of flexible tubing on which the needle is mounted becomes exposed from the holder to allow a degree of lateral movement of the holder relative to the needle.

None of the above inventions and patents, taken either singly or in combination, is seen to describe the instant invention as claimed.

SUMMARY OF THE INVENTION

The present invention a pivotal syringe needle holder for use with an injector. The syringe needle holder basically includes a hub and a ball. A needle is supported by the ball which, in turn, is movably supported by the hub so as to permit the needle to be angularly displaced relative to the hub.

The hub is engageable with the injector. The ball is captively received by the hub and is pivotally displaceable within the hub. The ball and hub are configured to form a ball and socket arrangement which cooperatively permits medicant to be communicated therethrough.

Upon engaging the hub and the injector, contact seal is formed between the ball and hub to prevent loss of medicant. The hub may further include a physical seal which may be provided supplemental to, or in place of, the contact seal.

The ball and hub have a needle passing therethrough. The needle provides a passage for medicant to flow therethrough. The ball is configured to tightly permit the passage of a needle therethrough, thereby prohibiting axial movement of the needle relative to the ball. Moreover, the needle may be affixed to the ball. A recess formed in the ball is dimensioned and configured to permit radial deflection of the needle within the ball. Sharp surfaces are minimized to reduce the risk of fracturing the needle through the movement of the ball.

The needle possess highly resilient characteristics that render the needle capable of being deflected and thereby permit the ball to be pivotally displaced. The needle further has opposingly disposed piercing tips. A first piercing tip is for use in piercing a carpule within the injector. A second piercing tip is intended for use in piercing a patient.

An alternative syringe needle holder is disclosed wherein a needle does not pass through the ball and hub but is threadably supported by the ball.

The hub includes a seat member and a clevis member. One side of the clevis is pivotally attached the seat member. A latch releasably attaches an opposite side of the clevis to the seat member so as to cooperatively form a socket configuration for receiving the ball. Upon engaging the clevis member and the seat member, a contact seal is formed between the ball and the seat and clevis.

The seat member includes a piercing tip extending therefrom. Upon engaging the seat member with an injector, the piercing tip engages a carpule supported by an injector. A bore passing through the seat member and the piercing tip permits medicant to be communicated from the carpule to the ball.

The ball includes a bore passing axially therethrough which remains in fluid communication with a recessed chamber in a concave surface formed in the seat member. Upon engaging a needle with the ball, a seal obstructing a bore is penetrated by the needle, which places the needle in fluid communication with the bore passing through the ball, thereby permitting medicant to be communicated from a carpule through the needle.

The ball is pivotally captivated between the seat member and the clevis member, forming a ball and socket arrangement. The ball may be manipulated to displace the needle relative to the injector. To manipulate the ball, the latch releases the clevis member from the seat member, thereby relieving tension against the ball. With the tension relieved, the ball and the needle attached thereto are free to be displaced relative to the hub. Once the desired placement of the ball and needle is achieved, the clevis member is reattached to the seat member, applying tension to the ball and maintaining the ball and needle in the desired position.

The first embodiment disclosed above is intended to be disposable. The second embodiment is intended to be non-disposable and is further intended to be used in combination with a disposable needle.

Accordingly, it is a principal object of the present invention to provide a syringe needle holder which is engageable with an injector and which permits a syringe needle to be pivotally displaced relative to the injector.

Another object is that fluid communication be permitted between a carpule contained within an injector and syringe needle holder to permit medicant to be communicated to the carpule.

It is another object that the syringe needle holder basically include a hub and a ball which are configured to cooperatively form a ball and socket arrangement which permits medicant to be communicated therethrough.

Another object is that a seal be formed between the ball and hub which prevents loss of medicant.

Yet another object is that the needle, or some portion thereof, be fixed axially relative to the ball to reduce the risk of the needle becoming detached from the ball and hub, yet be permitted to be radially deflectable relative to the ball and hub.

It is another object that a disposable needle be releasably attachable to the syringe needle holder.

Still another object is that the ball, and the needle attached thereto, be permitted to be substantially fixed and a desire location relative to the hub and injector to reduce the risk of an inadvertent displacement of the ball and, in turn, the needle.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
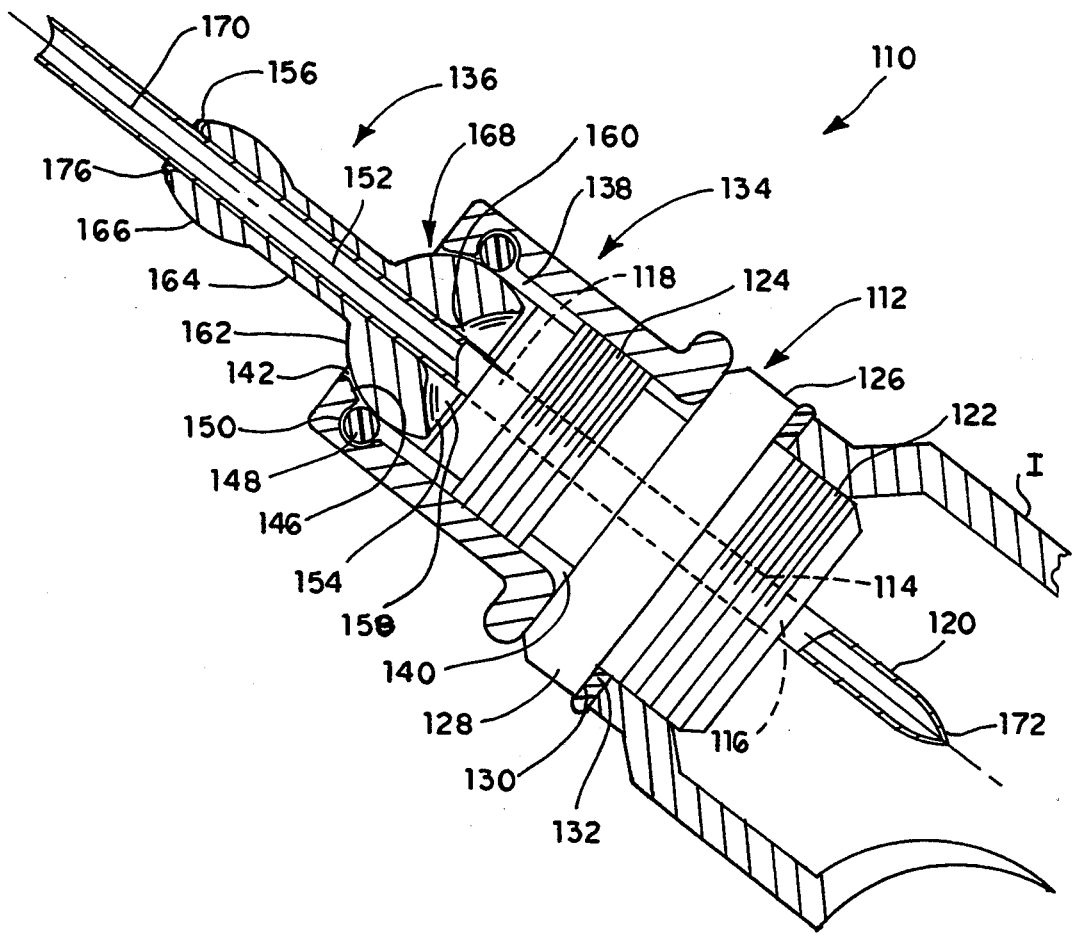
FIG. 1 is a partial sectional, partial environmental elevation of a syringe needle holder according to the present invention.

The present invention, as shown in FIG. 1, is a disposable, pivotal syringe needle holder 110. A coupling 112 is adapted to attach the needle holder 110 to an injector I, such as a dental syringe. The coupling 112 is cooperatively engageable with the injector I which, in turn, is cooperatively engageable with the syringe needle holder 110.

The coupling 112 has a bore 114 passing therethrough. The bore 114 forms a first opening 116 in a first end of coupling 112. The bore 114 further forms a second opening 118 in a second end of the coupling 112, opposite to the first end. This bore 114 permits provides a passage through which a needle 120 may loosely pass.

The first end includes an externally threaded member 122 which is threadably engageable with the body of the injector I. The second end includes a reduced diameter threaded portion 124 which is engageable with the syringe needle holder 110. An enlarged diameter medial portion 126 adjoins the externally threaded member 122 and the reduced diameter threaded portion 124.

The enlarged diameter medial portion 124 further forms a flange 128 having an abutting surface 130. A seal 132 is supported by the externally threaded member 122. Upon threadably engaging the coupling 112 and the body of the injector I, the seal 132 sealingly contacts the abutting surface 130 of the flange 128 and a corresponding abutting surface of the body of the injector I.

The syringe needle holder 110 basically includes a cap or hub 134 and a ball 136. A needle 120 is supported by the ball 136 which, in turn, is movably supported by the hub 134 so as to permit the needle 120 to be angularly displaced relative to the hub 134.

The hub 134 includes a bore 138 bounded by a peripheral wall. The hub 134 further includes a first end and a second end opposite the first end. A first cylindrical opening 140 is disposed at the first end of the hub 132 and a second, or reduced diameter, opening 142 is disposed at the second end of the hub 132.

The first cylindrical 140 opening defines a mouth. The mouth 140 is dimensioned and configured to receive the coupling 112. The bore 138 includes an internal thread 144 (see FIG. 2) located adjacent the mouth 140 of the bore 138. The internal thread 144 is matingly engageable with the reduced diameter threaded portion 124 (see FIG. 2) of the coupling 112.

The reduced diameter opening 142 is dimensioned and configured to provide a restrictive passage for the ball 136 therethrough. The bore 138 includes a radially extending, concave surface 146 located adjacent the reduced diameter opening 142 of the bore 138. The concave surface 146 has a shape which is complementary to that of the ball 136.

Upon engagement of the hub 134 and the coupling 112, a pressure is applied against the ball 136 by the coupling 112. This pressure forces the ball 136 into contact with the concave surface 146 located interiorly of the hub 134. The ball 136 and the concave surface 146 are preferably configured within such a close tolerance to one another that a contact seal is provided therebetween.

The hub 134 may further include a physical seal 148, such as the O-ring supported by the annular groove 150 in the inner peripheral wall of the hub 134. This physical seal 148 may be supplemental to, or in place of, the above mentioned contact seal.

The ball 136 includes an inner peripheral wall bounding a bore 152 passing axially through the ball 136. The ball 136 also includes a first end and a second end opposite the first end. A first, or enlarged diameter, opening 154 is located at the first end of the ball 136 and a second, or substantially uniformed diameter is located at the second end of the ball 136. The bore 152 is configured to tightly permit the passage of a needle 120 therethrough.

Figure 2:
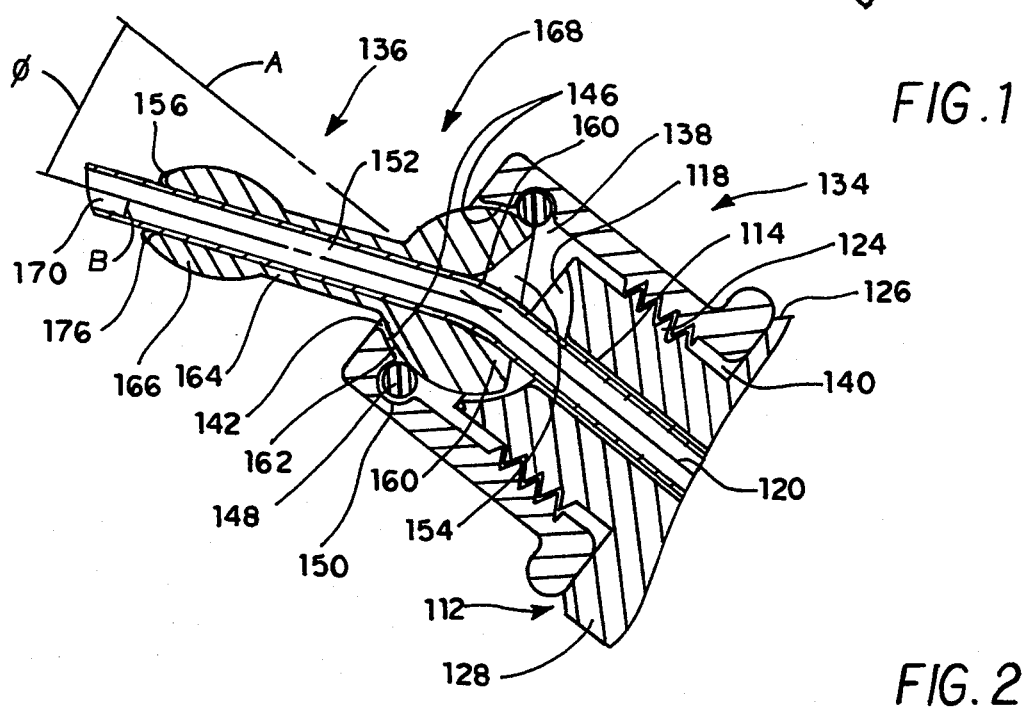
FIG. 2 is a partial sectional, partial environmental elevation of the syringe needle holder shown in FIG. 1 with the needle thereof offset.

The enlarged diameter opening 154 defines a concave recess 158 which essentially tapers into a conical shape 160. The concave recess 158 is dimensioned and configured to permit movement of a needle 120 therein, as is shown in FIG. 2.

It should be noted that the surfaces of the inner peripheral wall bounding the enlarged diameter opening 154 and the bore 152 are blunt so as to reduce the risk of fracturing a needle 120 therein. It should also be noted that the surface of the peripheral wall defining the uniform diameter opening 156 is blunt so as to reduce the risk of fracturing the needle 120 as well.

The ball 136 further includes an outer peripheral wall defining an enlarged, partially spherical member 162 located at the first end of the ball 136, an enlarged diameter tip 166 located at the second end of the ball 136, and an intermediate portion 164 adjoining the enlarged, partially spherical member 162 and the enlarged diameter tip 166 along a common axis.

The enlarged, partially spherical member 162 is pivotally captivated by the hub 134, forming a ball and socket arrangement 168. The enlarged diameter tip 166 facilitates as a guide element for controlling the movement of the enlarged, partially spherical member 162. The intermediate portion 164 functions as a leverage arm to render movement of the enlarged, partially spherical member 162 by the enlarged diameter tip 166.

The needle 120 according to this embodiment is a segment of conduit having a first end and a second end opposite the first end. The needle 120 is preferably formed of a stainless steel material. The needle 120 is further structure and configured to possess highly resilient characteristics that render the needle 120 capable of being deflected well within the range necessary to permit the ball 136 to pivot.

The needle 120 has a bore 170 passing therethrough. The bore 170 is bounded by a peripheral wall. A first opening is located at the first end of the needle 120 and a second opening is located at a second end of the needle 120. The ends of the needle 120 defining the first and second openings are each formed in the shape of a piercing tip 172, 174 (see FIG. 3). The first piercing tip 172 is permitted to pass through the bore 114 in the coupling 112 and is intended for use in piercing a carpule E within the injector I, similar to the carpule shown in FIG. 5. The second piercing tip 174 is intended for use in piercing a patient (not shown).

It is preferable that the needle 120 fit tightly within the bore 152 passing through the ball 136. Hence, should the needle 120 break within the ball 136, the needle 120 would be prevented from separating from the ball 136. Moreover, the needle 120 may be affixed or fused to the ball 136 to further reduce the risk of the needle 120 becoming separated from the ball 136. For example, the needle 120 may be soldered to the ball 136, such as shown in FIG. 1 wherein a solder joint 176 adjoins the needle 120 to the second end of the ball 136 about the uniform diameter opening 156.

Referring to FIGS. 1 and 2, the needle 120 may be directed as desired by manipulating the ball 136 relative to the hub 134. In FIG. 1, the ball 136 and needle 120 are shown in a first, or an initial, position. In this position, the needle 120 is in a relaxed posture and the axis of the bore 152 passing through the ball 136 defines a first longitudinal axis A.

In FIG. 2, the ball 136 is shown in a displaced posture, deflecting the needle 120 so as to displace the first end of the needle 120 relative to the first longitudinal axis A. In this position, the bore 152 passing through the ball 136 defines a second longitudinal axis B. A portion of the needle 120 within the ball 136 and extending from the second end of the ball 136 defines an axis which is coincident with the second longitudinal axis B.

The angle $\theta$ between the first longitudinal axis A and the second longitudinal axis B defines the angle of displacement of the needle 120. The desired angle of displacement should be limited to an angle of deflection which is within the tolerances established by the physical properties of the needle 120, such as an angle less then 45 degrees. In this way, the needle 120 is prohibited from being deflected to a position where the needle 120 may be fractured.

Figure 3:
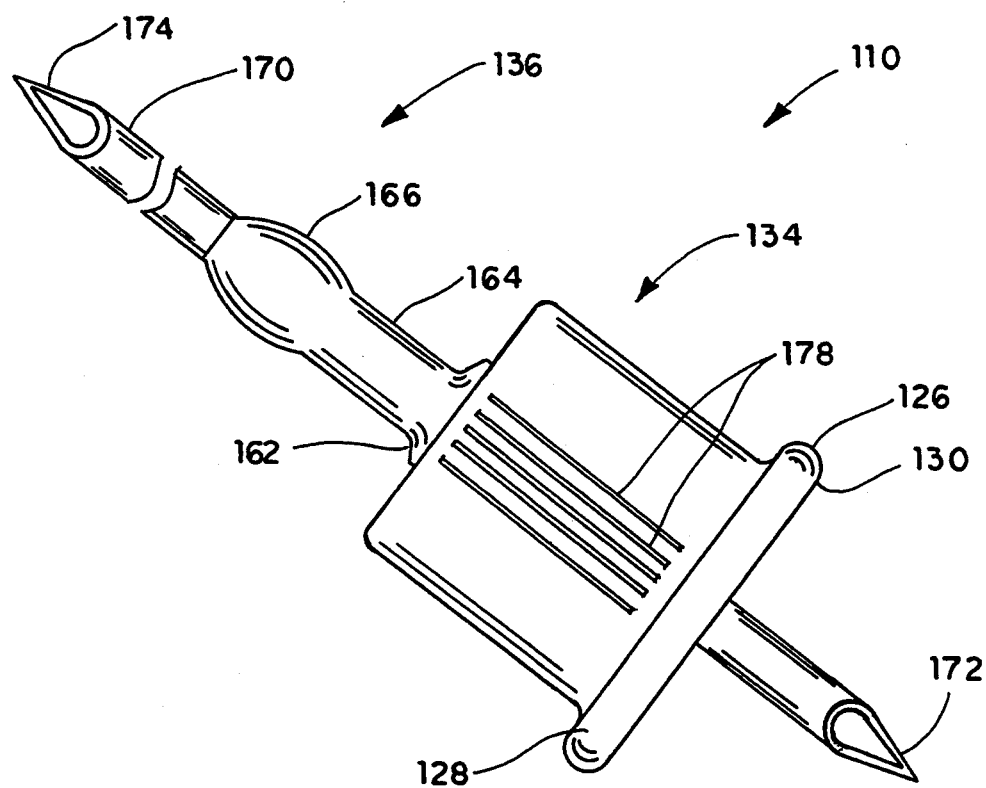
FIG. 3 is an elevation of the syringe needle holder shown in FIG. 1.

As shown in FIG. 3, the outer surface of the peripheral wall of the hub 134 is provided with a ribbed or traction surface 178. This traction surface 178 enhances the grip of the individual applying the hub 134 to the coupling 112 and thus aids in tightening the hub 134 securely to the coupling 112 so as to produce the desired seal between the surface of the ball 136 and the radially extending, concave surface 146 within the hub 134.

Figure 4:
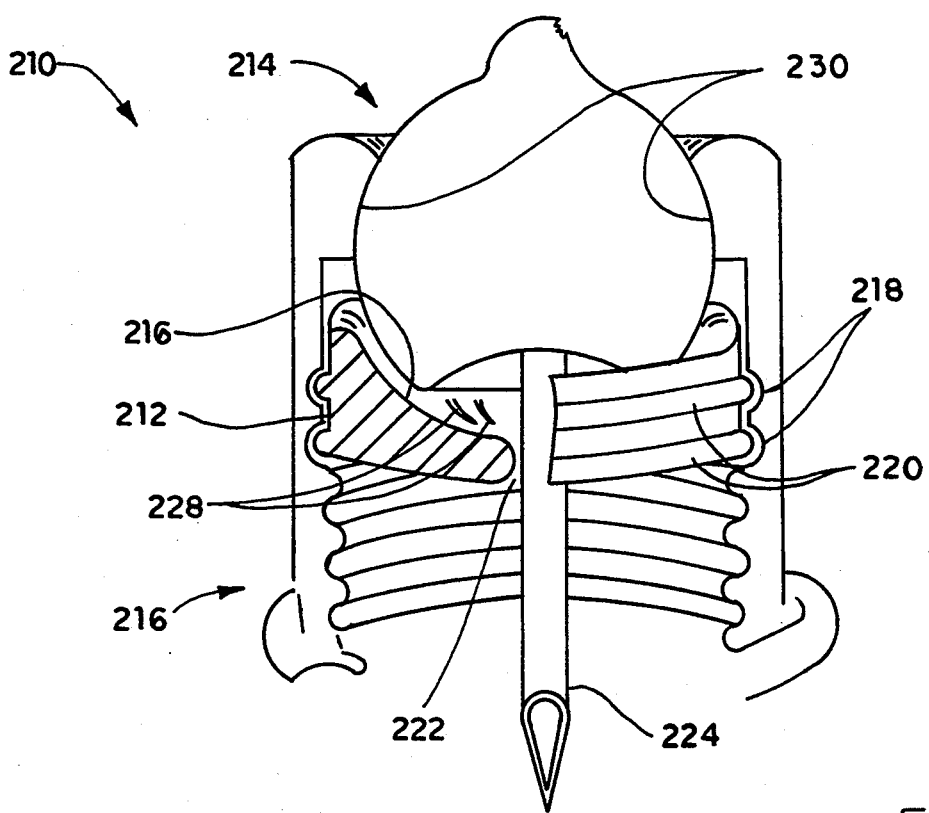
FIG. 4 is a partially cutaway elevation of an alternative syringe needle holder shown largely in elevation.

An alternative disposable syringe needle holder 210 is shown in FIG. 4. This syringe needle holder 210 includes a packing member 212 interposed between the ball 214 and the male counterpart (not shown) joining the hub 216 to the injector I. The packing member 212 may fit loosely within the hub 216 or may cooperatively engage the hub 216.

As shown in the drawing, the hub 216 includes a peripheral wall. The peripheral wall has an inner surface. A plurality of annular grooves 218 are located within the inner surface. The packing member 212 has an outer peripheral surface. A plurality of concentrically disposed protrusions 220 extend radially from the outer peripheral surface. Each of these protrusions 220 are cooperatively engageable with a respective one of the annular grooves 218 located within the inner surface of the peripheral wall of the hub 216. This configuration maintains the packing member 212 in a substantially fixed location within and relative to the hub 216.

The packing member 212 further includes an inner peripheral surface bounding a central bore 222 through which a needle 224 is permitted to pass. An upper concave surface 226 forms a substantially hemispherical seat or dish. This concave surface 226 may be provided with formations 228, such as the radially extending formations shown. These formations 228 are dimensioned and configured to resist undesirable movement of the ball 214 relative to the hub 216.

Upon engagement of the hub 216 with the male counterpart, a pressure is applied against the ball 214, forcing the ball 214 into contact with the concave surface 230 located interiorly of the hub 216. The ball 214 and the concave surface 226 are preferably configured so as to provide a contact seal therebetween.

In addition, the packing member 212 may be fabricated from an expansible material. Upon compression of the packing member 212 between the ball 214 and the male counterpart, a contact seal should be produced between the hub 216 and the male counterpart, between the hub 216 and the packing member 212, and between the male counterpart and the packing member 212. Such a configuration should further reduce the risk of loss of medicament.

Figure 5:
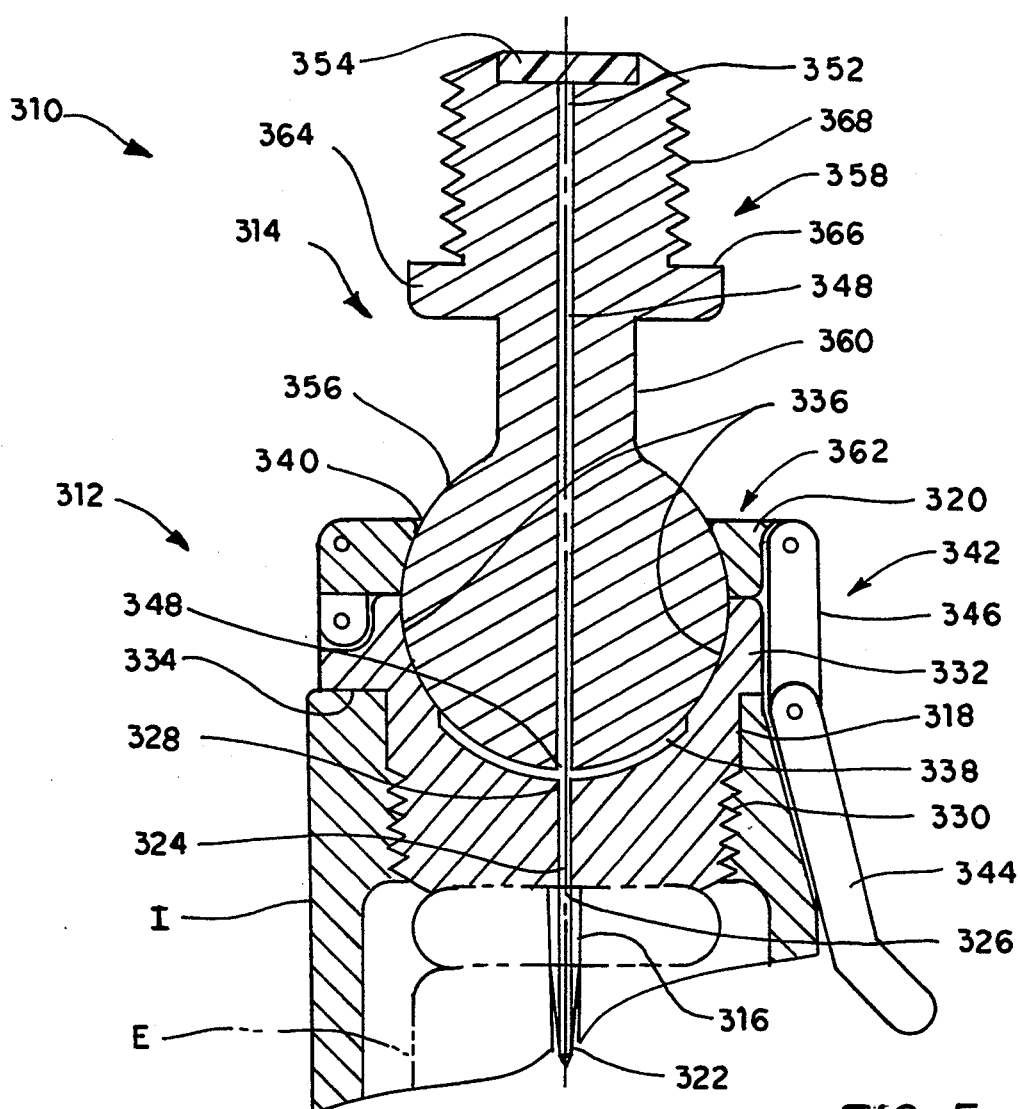
FIG. 5 is a partial sectional, partial environmental elevation of a second alternative syringe needle holder.
Figure 6:
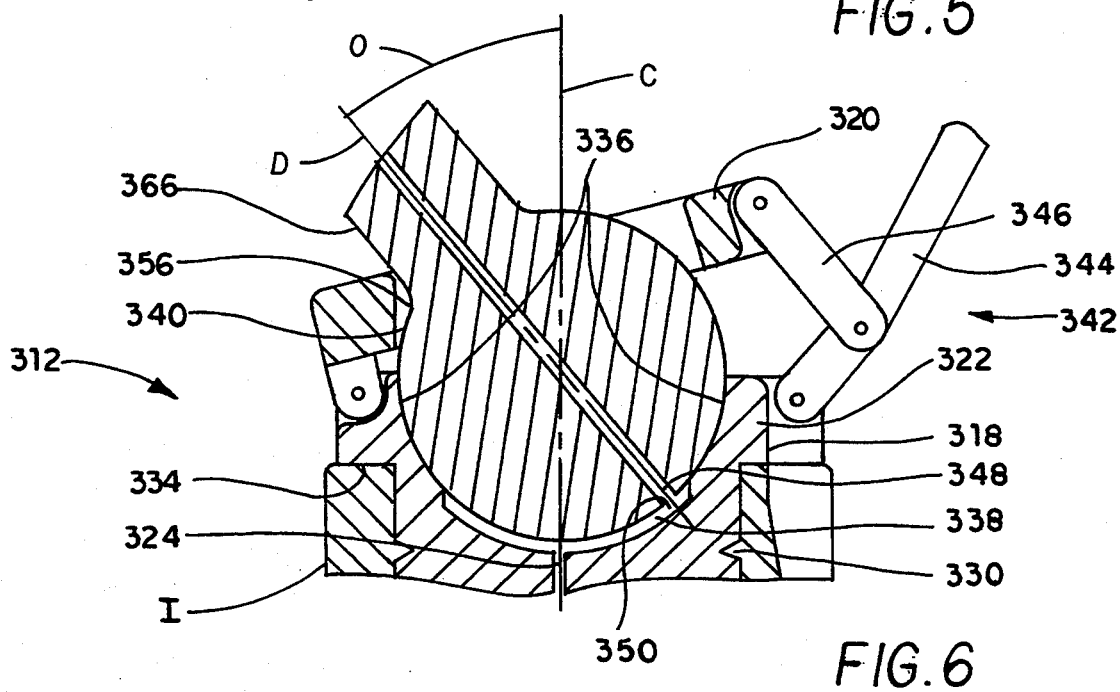
FIG. 6 is a partial sectional, partial environmental elevation of the second alternative syringe needle holder shown in FIG. 5 with the needle thereof offset.

Now referring to FIGS. 5 and 6, yet another alternative syringe needle holder 310 is shown. This syringe needle holder 310 includes a hub 312 and a ball 314. A needle 316 is supported by the ball 314 which, in turn, is movably supported by the hub 312.

The hub 312 includes a seat member 318 and a clevis member 320. A first side of the clevis member 320 is pivotally or hingedly attached to a first side of the seat member 318. A second side of the clevis member 320 is releasably attachable to a second side of the seat member 318 so as to form a socket configuration for receiving the ball 314.

The seat member 318 includes a first end and a second end opposite the first end. A piercing tip 322 extends from the first end of the seat member 318. Upon engaging the seat member 318 with an injector I, the piercing tip 322 engages a carpule E supported by an injector I. A bore 324 bounded by a peripheral wall passes through the seat member 318 and the piercing tip 322.

A first opening 326 is disposed at a first end of the piercing tip 322 and a second opening 328 is disposed at the second end of the seat member 318. Medicant from the carpule E within the injector I is permitted to enter into the first opening 326, pass through the bore 324, and exit through the second opening 328.

An externally threaded member 330 is located at the first end of the seat member 318. The externally threaded member 330 is dimensioned and configured to matingly engage the internal threads within the nose of the injector I.

An enlarged diameter portion 332 is located at the second end of the seat member 318. The enlarged diameter portion 332 includes an abutment surface 334 which abuttingly engages an abutment surface located at the end of the nose of the injector I.

A radially extending concave surface 336 defining a seat is formed in the second end of the seat member 318. The concave surface 336 has a shape which is complementary to that of the ball 314. The bottom of the seat 336 is provided with a recessed chamber 338 which is in fluid communication with the bore 324 passing through the seat member 318.

The clevis member 320 has a central opening 340 therethrough bounded by an inner peripheral wall. Upon closing the clevis member 320, the concave surface 336 in the second end of the seat member 318 and central opening 340 through the clevis member 320 cooperate to form a hemispherical chamber. The central opening 340 is dimensioned and configured to provide a restrictive passage for the ball 314 therethrough.

Upon engaging the clevis member 320 and the seat member 318, a pressure is applied against the ball 314 by the seat member 318 forcing the ball 314 into contact with the inner peripheral wall located interiorly of the clevis member 320, thus forming a contact seal between the ball 314 and the seat member 318 and the ball 314 and the clevis 318.

The hub 312 further includes an over-center latch 342 for releasably attaching the clevis 320 to the seat member 318. The over-center latch 342 includes an arm 344 and a link 346. The arm 344 is pivotally attached to the second side of the seat member 318. The link 346 pivotally connects the second side of the clevis 320 to the arm 344.

The ball 314 according to this embodiment includes an inner peripheral wall bounding a bore 348 passing axially through the ball 314. The ball 314 also includes a first end and a second end opposite the first end. A first opening 350 is located at the first end of the ball 314 and a second opening 352 is located proximate the second end of the ball 314. The first opening 350 remains in fluid communication with the recessed chamber 338 in the bottom of the concave surface 336 formed in the seat member 318. The second opening 352 is obstructed by a seal 354 which is penetrable by a needle 315 upon engaging a needle 316 with the ball 314.

Similar to that of the aforementioned embodiments 110, 210, the ball 314 according to this embodiment of needle holder 310 further includes an outer peripheral wall defining an enlarged hemispherical member 356 located at the first end of the ball 314, an enlarged diameter tip 358 located at the second end of the ball 314, and an intermediate portion 360 adjoining the enlarged, hemispherical member 356 and the enlarged diameter tip 358 along a common axis.

The enlarged hemispherical member 356 is pivotally captured between the seat member 318 and the clevis member 320, forming a ball and socket arrangement 362. The enlarged diameter tip 358 includes a flange 364 having an abutment surface 366 and an externally threaded portion 368. The flange 364 is located adjacent the intermediate portion 360 of the ball 314. The externally threaded portion 368 is located adjacent the flange 364 and opposite the intermediate portion 360.

The externally threaded portion 368 is matingly engageable with a needle hub (not shown) which is to be distinguished from the hub 312 of the syringe needle holder 310. The abutment surface 366 of the flange 364 of the enlarged diameter tip 358 of the ball 314 contacts an abutment surface at the first end of the hub of a needle, thus forming a contact seal therebetween.

The needle hub supports a needle (not shown) having a bore passing therethrough. A first opening is located at the first end of the needle and a second opening is located at a second end of the needle. The first and second openings are in fluid communication with the bore passing through the needle. The ends of the needle defining the first and second openings are each formed in the shape of a piercing tip.

Upon engagement of a needle with the ball, the first piercing tip of the needle penetrates the seal obstructing the opening 352 at the second end of the ball 314. This places the bore passing through the needle in fluid communication with the bore 348 passing through the ball 314.

In use, the second piercing tip of the needle is intended for use in piercing a patient (not shown). Upon depressing the plunger (not shown) of the injector I, medicant flows through the seat member 318, the ball 314, and the needle into the patient. After using the needle, the needle may be disengaged from the ball 314 and properly discarded, and the syringe needle holder 310 may be sterilized and reused.

As shown in FIG. 5, the ball 314 is captively retained by the seat and clevis members 318 and 320 in a first, or an initial, position. In this position, the ball 314 defines a first longitudinal axis C. Similar to the syringe needle holder 110 described above, the ball 314 in accordance with this embodiment may be manipulated to displace the needle relative to the injector I.

To manipulate the ball 314, the arm 344 of the over-center latch 342 is raised, as is shown in FIG. 6, relieving tension applied by the clevis member 320 against the ball 314. With the tension relieved, the ball 314 and the needle are free to be displaced, as is shown in FIG. 6. In this displaced posture, the bore 348 passing through the ball 314 defines a second longitudinal axis D. Moreover, the needle engaging the ball 314 defines an axis which is coincident with the second longitudinal axis D.

The angle $\phi$ between the first longitudinal axis C and the second longitudinal axis D defines the angle of displacement of the needle. The desired angle of displacement should be limited to an angle of deflection which is within the tolerances established by the physical properties of the needle. In this way, the needle is prohibited from being deflected to a position where the needle may be fractured.

It is to be understood that the present invention is not limited to the embodiments described above, but encompasses any and all embodiments within the scope of the following claims.

We claim:

1. A syringe needle holder for use in supporting a syringe needle, comprising:
    a hub;
    a ball movably supported by said hub, said ball including at least means for supporting a needle;
    wherein said ball is further structured and configured to have a concavity therein through which the needle passes and in which the needle is enabled to be radially deflected;
    said needle supporting means further including a bore passing through said ball, said bore being dimensioned and configured to tightly receive the needle so as to substantially prevent axial displacement of the needle relative to the ball; and
    means for providing a passageway for fluid communication through said hub, said ball, and said needle.

2. The syringe needle holder according to claim 1, further including
    means for fixedly attaching a portion of the needle to the ball.

3. The syringe needle holder according to claim 1, wherein said needle supporting means includes
    a means for releasably attaching the needle to the ball.

4. A syringe needle holder for use in supporting a syringe needle having a bore passing therethrough and for use in combination with an injector configured to carry a carpule having medicament therein, said syringe needle holder comprising:
    a ball and socket arrangement including at least:
        a hub having a concave surface therein; and
        a ball being supported by said hub and being matingly engageable with a concave surface within said hub, said ball including at least:
            means for supporting a needle including a first bore passing through said ball, said first bore being dimensioned and configured to tightly receive the needle so as to substantially prevent axial displacement of the needle relative to the ball;
    means for attaching said ball and socket arrangement to the injector; and
    means for providing a passageway for fluid communication from the carpule in the injector through said ball and socket arrangement, and further through the needle.

5. The syringe needle holder according to claim 4, wherein said attaching means includes
    a coupling having a first end being matingly engageable with the injector; and
    a second end opposite said first end, said second end being matingly engageable with said hub.

6. The syringe needle holder according to claim 5, wherein
    said first end of said coupling is structured so as to be threadably engageable with the injector; and
    said second end of said coupling is structured so as to be threadably engageable with said hub.

7. The syringe needle holder according to claim 4, wherein said passageway means includes
    means defining a second bore passing through said hub, said second bore being dimensioned and configured to loosely receive the needle therethrough, and wherein
    the needle is structured to extend through both said ball and said hub and further into the carpule within the injector, thus providing a passage for the medicament within the carpule through the needle and, in turn, through said ball and said hub.

8. The syringe needle holder according to claim 4, wherein said passageway means includes
    a piercing tip being extendable from said hub into the carpule in the injector, said piercing tip having a first bore passing therethrough from said carpule to said hub;

means defining a second bore passing through said hub, said second bore being in continuous fluid communication with said first bore; and means defining a third bore passing through said ball, said third bore simultaneously and continuously being in fluid communication with said second bore and said first bore passing through the needle.

9. A syringe needle holder for use in supporting a syringe needle and in combination with an injector configured to carry a carpule having medicament therein, said syringe needle holder comprising:

a ball and socket arrangement including at least:

a hub having a concave surface therein; and a ball being matingly engageable with said concave surface of said ball, said ball further being captively and movably supported by said hub, said ball including at least means for supporting a needle;

means for providing a seal between said hub and said ball;

means for attaching said ball and socket arrangement to the injector; and means for providing a passageway for fluid communication from the carpule in the injector through said ball and socket arrangement, and further through the syringe needle, wherein said fluid communication means includes a piercing tip being extendable from said hub into the carpule in the injector, said piercing tip having a first bore passing therethrough from said carpule to said hub;

means defining a second bore passing through said hub, said second bore being in continuous fluid communication with said first bore; and means defining a third bore passing through said ball, said third bore simultaneously and continuously being in fluid communication with said second bore and said bore passing through said piercing tip.

10. The syringe needle holder according to claim 9, wherein said attaching means includes a coupling having a first end being matingly engageable with the injector; and a second end opposite said first end, said second end being matingly engageable with said hub.

11. The syringe needle holder according to claim 10, wherein said first end of said coupling is structured so as to be threadably engageable with the injector; and said second end of said coupling is structured so as to be threadably engageable with said hub.

12. The syringe needle holder according to claim 9, wherein said needle supporting means includes means defining a first bore passing through said ball, said first bore being dimensioned and configured to tightly receive the needle so as to substantially prevent axial displacement of the needle relative to the ball.

13. The syringe needle holder according to claim 12, wherein said fluid communication means includes means defining a second bore passing through said hub, said second bore being dimensioned and configured to loosely receive the syringe needle therethrough, and wherein the syringe needle is structured to extend through both said ball and said hub and further into the carpule within the injector, thus providing a passage for the medicament within the carpule through the syringe needle and, in turn, through said ball and said hub.

* * * * *